United States Patent [19]

Irwin

[11] Plant 4,067

[45] June 28, 1977

[54] KALANCHOE PLANT

[76] Inventor: Lawrence T. Irwin, P.O. Box 657, Canyon, Tex. 79015

[21] Appl. No.: 693,882

[22] Filed: June 7, 1976

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Frank B. Robb

EXEMPLARY CLAIM

1. A new and distinct variety of Kalanchoe plant, substantially as herein shown and described, characterized particularly as to novelty by the unique combination of tall, vigorous growth habit of from 16 inches to 20 inches in height; its medium large size flexible foliage of fern green color; the profusion of unique crimson color flowers carried on sturdy stems 6 inches above the foliage; the absence of an eye in the flowers; its vigorous free breaking habit; and its adaptability to year round flowering by photoperiod manipulation producing a large pot plant from a single cutting.

1 Drawing Figure

The present invention relates to a new and distinct variety of Kalanchoe plant which was originated by me in a very extensive program of breeding and selection, by crossing the Kalanchoe variety known as "Exotic" (U.S. Plant Pat. No. 3,149), availing of its qualities as a seed parent, and an unpatented variety known as "Ramona", which variety is the pollen parent.

As a result of this breeding and selection, I have produced a new and improved Kalanchoe variety which is distinguished from its parents, as well as from all other Kalanchoe varieties of which I am aware, as evidenced by the following unique combination of principal characteristics which are outstanding in the new variety and which make it a valuable addition to the line of Kalanchoe varieties which is presently commercially available:

1. A tall, upright, vigorous habit with plants of 16 inches to 20 inches in height;
2. The profusion of flowers carried on a sturdy stem 6 inches above the foliage;
3. The vigorous free breaking habit;
4. The unique crimson color and absence of an eye;
5. Its medium large sized flexible foliage of fern green color;
6. Its adaptability to year round flowering, determined by photoperiod manipulation; and
7. Its ability to produce a large pot plant from a single cutting.

Asexual reproduction of my new Kalanchoe variety by means of cuttings, as performed by me in my greenhouses located at Canyon, Tex., shows that the foregoing characteristics and distinctions come true and are established and transmitted through succeeding propagations.

In comparison with the parent varieties, it is notable that it is taller, more upright and vigorous than either parent. It flowers about the same time as "Exotic" but 10 to 14 days before "Ramona", the former being the seed parent and the latter the pollen parent as previously noted.

My new variety has a crimson color which is distinctive from either parent and as compared to "Exotic", can be grown with one cutting for a pot and produce a large saleable plant when so grown which "Exotic" will not do.

The accompanying drawing shows a typical blooming plant of my new variety, as well as a close-up view of the flowers, as depicted in color as nearly true as it is possible to make the same in a color illustration of this character.

The following is a detailed description of my new variety, with color terminology in accordance with Maerz and Paul Dictionary of Color, as contained in Exotica No. 3 by A. B. Graf, except where general color terms of ordinary dictionary significance are equally or more commonly applicable:

Parentage: Seedling.

*Seed parent.*—"Exotic" (U.S. Plant Pat. No. 3,149).

*Pollen parent.*—"Ramona" an unpatented hybrid.

Propagation: Holds its distinguishing characteristics through successive propagation by cuttings.

Locality where grown and observed: Canyon, Tex.

Plant:

*Form.*—Tall; upright.

*Growth habit.*—Much branched; upright; medium; vigorous; 16 inches to 20 inches tall.

*Rooting habit.*—Coordinate; roots easily from any part of the stem forming a fibrous root system.

*Blooming habit.*—Natural flowering occurs approximately Dec. 15 and since it is a short day plant.

*Blooming season.*—As a short day plant, it can be flowered year round with photoperiod control as evidence of its suitability for forcing, it blooms in about 12 weeks as compared to other varieties.

Foliage:

*Size.*—Large.

*Quantity.*—Abundant.

*Color.*—New foliage — Upper side — (83) Fern Green; Under side — (83−). Old foliage — Upper side — (83+); Under side — (83).

*Texture.*—Upper side — Glossy and smooth. Under side — Smooth.

Disease Resistance: My new variety as compared to other new hybrids has about the same disease resistance, but it is definitely more resistant than known standard varieties to such diseases as they are accustomed to having, the comparison being made with other varieties in the greenhouse at Canyon, Tex., under the same conditions.

Flowers: Pistillate; staminate; perfect complete.

*Size.*—Diameter — 0.5 cm; Depth — 1.2 cm. Petals — Length — 0.7 cm; Width — 0.5 cm.

*Form.*—Umbel.

*Color.*—Upper side — New flowers — Crimson (32−); Old flowers — Turning carmine red (31+). Under side — New flowers — (30+). Throat of corolla — Does not have a distinct eye.

*Blooming period.*—from 4 to 5 weeks.

Fruit: None.

Hardiness: Good in range of 50° F to 100° F as grown in greenhouse, but would not be hardy in outside conditions in temperate climates.

General observations: The new variety has the distinctively good desirable qualities of a pot plant, with a flower color and a vigorous, upright form which makes it distinctive from all other Kalanchoe plants; its ability to flower in 12 weeks from a single cutting also distinguishes it from other Kalanchoe varieties.

I claim:

1. A new and distinct variety of Kalanchoe plant, substantially as herein shown and described, characterized particularly as to novelty by the unique combination of tall, vigorous growth habit of from 16 inches to 20 inches in height; its medium large size flexible foliage of fern green color; the profusion of unique crimson color flowers carried on sturdy stems 6 inches above the foliage; the absence of an eye in the flowers; its vigorous free breaking habit; and its adaptability to year round flowering by photoperiod manipulation producing a large pot plant from a single cutting.

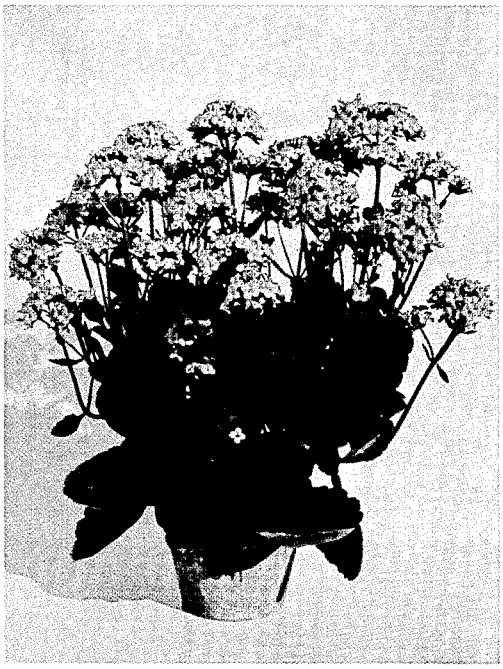
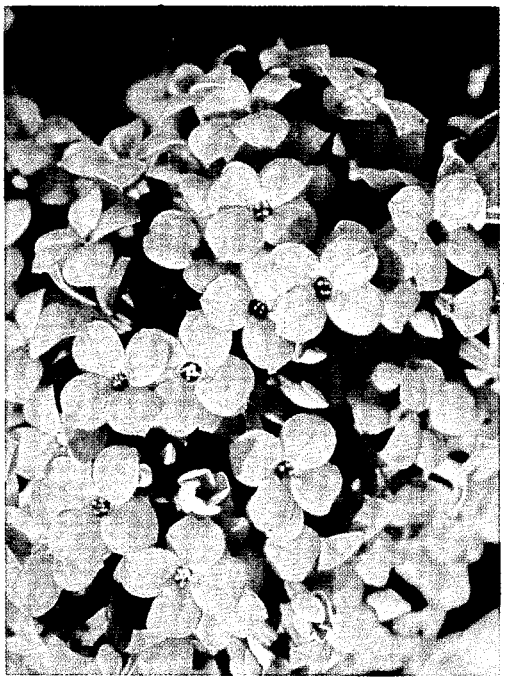

* * * * *